United States Patent [19]
Barry et al.

[11] Patent Number: 6,123,925
[45] Date of Patent: *Sep. 26, 2000

[54] ANTIBIOTIC TOOTHPASTE

[75] Inventors: John E. Barry, Derry, N.H.; Jeffrey A. Trogolo, Boston, Mass.

[73] Assignee: HealthShield Technologies L.L.C., West Hartford, Conn.

[*] Notice: This patent issued on a continued prosecution application filed under 37 CFR 1.53(d), and is subject to the twenty year patent term provisions of 35 U.S.C. 154(a)(2).

[21] Appl. No.: 09/123,755

[22] Filed: Jul. 27, 1998

[51] Int. Cl.$^7$ ............................. A61K 7/16; A61K 33/30; A61K 33/34; A61K 33/38

[52] U.S. Cl. ........................... 424/49; 424/617; 424/618; 424/630; 424/642

[58] Field of Search ............................... 424/49–58

[56] References Cited

U.S. PATENT DOCUMENTS

| | | | |
|---|---|---|---|
| 3,881,529 | 5/1975 | Mannara | 141/100 |
| 4,349,533 | 9/1982 | Dent et al. | 424/52 |
| 4,559,223 | 12/1985 | Fox, Jr. | 424/48 |
| 4,627,974 | 12/1986 | Lynch | 424/48 |
| 4,775,585 | 10/1988 | Hagiwara et al. | 428/323 |
| 4,826,676 | 5/1989 | Gioffre et al. | 424/52 |
| 4,906,464 | 3/1990 | Yamamoto et al. | 424/78 |
| 4,911,898 | 3/1990 | Hagiwara et al. | 423/118 |
| 4,911,899 | 3/1990 | Hagiwara et al. | 423/118 |
| 4,911,927 | 3/1990 | Hill et al. | 424/443 |
| 4,938,955 | 7/1990 | Niira et al. | 424/79 |
| 4,938,958 | 7/1990 | Niira | 424/79 |
| 4,986,288 | 1/1991 | Kent et al. | 132/321 |
| 5,009,898 | 4/1991 | Sakuma et al. | 424/618 |
| 5,035,349 | 7/1991 | Donahue | 222/107 |
| 5,098,711 | 3/1992 | Hill et al. | 424/401 |
| 5,102,401 | 4/1992 | Lambert et al. | 604/264 |
| 5,151,122 | 9/1992 | Atsumi et al. | 106/35 |
| 5,165,913 | 11/1992 | Hill et al. | 424/49 |
| 5,180,585 | 1/1993 | Jacobson et al. | 424/405 |
| 5,292,528 | 3/1994 | Mori et al. | 424/54 |
| 5,296,238 | 3/1994 | Sugiura et al. | 424/604 |
| 5,324,505 | 6/1994 | Kornettka et al. | 424/49 |
| 5,330,748 | 7/1994 | Winston et al. | 424/49 |
| 5,405,644 | 4/1995 | Ohsumi et al. | 427/2.31 |
| 5,441,717 | 8/1995 | Ohsumi et al. | 423/306 |
| 5,455,024 | 10/1995 | Winston et al. | 424/52 |
| 5,503,851 | 4/1996 | Mank et al. | 424/489 |
| 5,560,517 | 10/1996 | Creeth et al. | 222/92 |
| 5,603,921 | 2/1997 | Bowen | 424/49 |
| 5,648,403 | 7/1997 | Martin | 523/117 |
| 5,665,333 | 9/1997 | Homola et al. | 424/54 |
| 5,688,492 | 11/1997 | Galley et al. | 424/49 |
| 5,697,203 | 12/1997 | Niwa et al. | 53/510 |
| 5,700,449 | 12/1997 | Katayama et al. | 424/49 |
| 5,711,935 | 1/1998 | Hill et al. | 424/49 |
| 5,714,430 | 2/1998 | Gehrer et al. | 502/347 |
| 5,714,445 | 2/1998 | Trinh et al. | 510/103 |
| 5,761,935 | 6/1998 | Adelmeyer | 70/55 |
| 5,769,638 | 6/1998 | Torabinejad et al. | 433/228.1 |
| 5,817,325 | 10/1998 | Sawan et al. | 424/411 |
| 5,849,311 | 12/1998 | Sawan et al. | 424/406 |

FOREIGN PATENT DOCUMENTS

| | | | |
|---|---|---|---|
| 136064 | 4/1970 | Czech Rep. | |
| 297563 | 1/1989 | European Pat. Off. | |
| 0 723 773 A1 | 7/1996 | European Pat. Off. | A61K 7/16 |
| 775670 | 5/1997 | European Pat. Off. | |
| 2-142711 | 5/1990 | Japan | A61K 6/08 |
| 03002113 | 1/1991 | Japan | |
| 03099007 | 4/1991 | Japan | |
| 5-032530 | 2/1993 | Japan | A61K 7/16 |
| 05163125 | 6/1993 | Japan | |
| 5-163125 | 6/1993 | Japan | A61K 7/16 |
| 5163125 | 6/1993 | Japan | |
| 06122617 | 5/1994 | Japan | |
| 06211619 | 8/1994 | Japan | |
| 07017821 | 1/1995 | Japan | |
| 08119821 | 5/1996 | Japan | A61K 6/08 |
| 08333210 | 12/1996 | Japan | |
| 09323912 | 12/1997 | Japan | A61K 6/06 |
| 09323936 | 12/1997 | Japan | |
| 9324103 | 12/1993 | WIPO | |
| WO 96/39202 | 12/1996 | WIPO | |
| WO 98/55043 | 12/1998 | WIPO | |

OTHER PUBLICATIONS

Terashita, Keijiro, *Funtai oyobi Funmatsu Yakin* 44(8), 740–745 (1997) Abstract only.

Kitahara, Minoru, *Koku Eisei Gakkai Zasshi* 46(1), 80–94 (1996) Abstract only.

Opperman The Effect of Organic and Inorganic Ions on the Acidogenicity of Dental Plaque Tooth Surf. Interact. Prev Dent Proc Workshop 1981 Mtg Date 1980 3–16.

*Primary Examiner*—Shep K. Rose
*Attorney, Agent, or Firm*—Darby & Darby

[57] ABSTRACT

An antibiotic toothpaste is formulated with an inorganic antibiotic metal containing composition that is present in an amount effective to impart substantial antimicrobial activity within the normal time for brushing teeth.

18 Claims, No Drawings

ANTIBIOTIC TOOTHPASTE

FIELD OF THE INVENTION

This invention relates to toothpaste exhibiting antimicrobial activity.

BACKGROUND OF THE INVENTION

Toothpaste formulations have been recently developed that exhibit antibiotic properties. Such formulations inhibit the growth of plaque, and consequently the advent of gum disease. For example, formulations described in U.S. Pat. No. 4,627,974 containing monoalkyl and dialkyl ethers of dianhydrohexitols are said to be effective in reducing plaque accumulation caused by bacteria.

Currently, a commercially available toothpaste employs the organic compound triclosan as an antibiotic agent. Triclosan is believed to quickly kill relevant bacteria during normal toothbrushing and leave a residue which exhibits long-lasting antimicrobial activity.

However, triclosan is an organic compound, and therefore suffers from the disadvantage that antibiotic resistance can develop over time with continued use. Furthermore, triclosan is suspected of inducing skin irritation.

A number of metal ions have been shown to possess antibiotic activity, including silver, copper, zinc, mercury, tin, lead, bismutin, cadmium, chromium and thallium ions. These antibiotic metal ions are believed to exert their effects by disrupting respiration and electron transport systems upon absorption into bacterial or fungal cells. Antimicrobial metal ions of silver, gold, copper and zinc, in particular, are considered safe for in vivo use. Antimicrobial silver ions are particularly useful for in vivo use due to the fact that they are not substantially absorbed into the body.

These ions, however, cannot be practically employed in current toothpaste formulations because the formulations contain sulfates and phosphates that inactivate the antibiotic activity of the ions.

Antibiotic zeolites have been prepared by replacing all or part of the ion-exchangeable ions in zeolite with ammonium ions and antibiotic metal ions, as described in U.S. Pat. Nos. 4,938,958 and 4,911,898. Such zeolites have been incorporated in antibiotic resins (as shown in U.S. Pat. Nos. 4,938,955 and 4,906,464) and polymer articles (U.S. Pat. No. 4,775,585). Polymers including the antibiotic zeolites have been used to make refrigerators, dish washers, rice cookers, plastic film, chopping boards, vacuum bottles, plastic pails, and garbage containers. Other materials in which antibiotic zeolites have been incorporated include flooring, wall paper, cloth, paint, napkins, plastic automobile parts, catheters, bicycles, pens, toys, sand, and concrete. Examples of such uses are described in U.S. Pat. Nos. 5,714,445; 5,697,203; 5,562,872; 5,180,585; 5,714,430; and 5,102,401. These applications, however, involve slow release of antibiotic silver from the zeolite particles. In toothpaste formulations, on the other hand, the antibiotic action must be exerted very quickly, i.e, during the fifteen to thirty second duration of a normal toothbrushing.

There is therefore a need for an antibiotic toothpaste formulation that avoids use of organic compounds that can induce development of resistant bacterial strains.

There is also a need for a toothpaste formulation that leaves an effective antibiotic residue that continues to kill plaque-forming bacteria for a substantial period after application.

SUMMARY OF THE INVENTION

The present invention relates to antibiotic toothpaste formulations containing an inorganic antibiotic metal composition that is present in an amount effective to impart substantial antimicrobial activity within the normal time for brushing teeth. The metal is non-toxic. The formulation preferably contains a barrier layer that isolates the composition from ingredients in the formulation that are capable of inactivating the antibiotic metal. In a preferred embodiment, the inorganic antibiotic metal composition is a ceramic particle containing an antibiotic metal.

DETAILED DESCRIPTION OF THE INVENTION

All patent applications, patents, patent publications, and literature references cited in this specification are hereby incorporated by reference in their entirety. In the case of inconsistencies, the present description, including definitions, is intended to control.

According to the present invention, an inorganic antibiotic metal containing composition is incorporated in a toothpaste formulation to provide quick, non-toxic antimicrobial action without the possibility, associated with organic compounds of the prior art, of development of antibiotic resistance or irritation. The use of a silver containing composition in particular allows an exceptionally safe, non-toxic and effective toothpaste to be formulated.

In the preferred embodiment, antibiotic ceramic particles are formulated in the toothpaste to provide antimicrobial activity. The toothpaste formulation provides antibiotic action that is at least as long lasting as presently used agents, such as triclosan, but avoids use of an organic antibiotic. Development of resistant bacterial strains is avoided. Furthermore, it has been determined that such a toothpaste formulation is able to adequately kill microorganisms during the time required for a normal toothbrushing.

This has been found to be true even when the particles are separated by a barrier layer from the portion of the toothpaste containing inactivating ingredients. For example, it has been found that silver containing zeolite that is incorporated in a polymer to separate the silver from phosphates and sulfates, releases silver upon normal brushing at a sufficient rate to quickly impart substantial antimicrobial action to the toothpaste.

It has also been found that a residue of antibiotic silver is retained on the surface of commonly used antibiotic zeolites that is especially effective at imparting quick antimicrobial action. At the same time, particles retained on the teeth and on or in the gums following brushing continue to slowly release non-exchanged antibiotic metal for an extended period.

In one embodiment of the invention, the inorganic antibiotic metal containing composition is an antibiotic metal salt. Such salts include silver acetate, silver benzoate, silver carbonate, silver iodate, silver iodide, silver lactate, silver laurate, silver nitrate, silver oxide, silver palmitate, silver protein, and silver sulfadiazine. Silver nitrate is preferred. These salts are particularly quick acting, as no release from ceramic particles is necessary for the toothpaste to function antimicrobially.

The toothpaste formulation allows the inorganic antibiotic metal containing composition to be incorporated without deactivating the antibiotic properties of the antibiotic metals as a result of contact with conventional agents employed in toothpaste formulations, such as sodium lauryl sulfate and trisodium phosphate. This is accomplished by isolating the inorganic antibiotic metal containing composition from these agents using a barrier composition, such as polymer compositions that are described in further detail below.

Alternately, the antibiotic metal containing composition is isolated from other ingredients using packaging wherein the packaging provides a physical barrier between the metal containing composition and the portion of the formulation containing agents that have the potential to deactivate the antibiotic metals.

The ceramics employed in the antibiotic ceramic particles of the present invention include zeolites, hydroxyapatite, zirconium phosphates or other ion-exchange ceramics. Zeolites are preferred, and are described in the preferred embodiments referred to below. Hydroxyapatite particles containing antimicrobial metals are described, e.g., in U.S. Pat. No. 5,009,898. Zirconium phosphates containing antimicrobial metals are described, e.g., in U.S. Pat. Nos. 5,296,238; 5,441,717; and 5,405,644.

Toothpaste containing non-antibiotic zeolites, wherein the zeolites are conventionally used for abrasive purposes, is described, for example, in U.S. Pat. No. 4,349,533. The formulation described therein is suitable for preparing the antibiotic toothpaste formulation of the invention, however, the conventional zeolites described in the '533 patent (used only for their abrasive properties) can be substituted for by the inorganic antibiotic metal containing composition. The inorganic antibiotic metal containing composition is separated from other inactivating ingredients by a barrier layer.

Other conventional toothpaste formulations can be employed to make the formulation of the invention, adding the antimicrobial composition in an effective amount. Toothpaste formulations employed to make the formulation of the invention can include conventional ingredients such as chalk, dicalcium phosphate dihydrate, sorbitol, water, hydrated aluminum oxide, precipitated silica, sodium lauryl sulfate, sodium carboxymethyl cellulose, flavoring, sorbitan monooleate, sodium saccharin, tetrasodium pyrophosphate, methyl paraben, propyl paraben. One or more coloring agents, e.g. FD&C Blue, can be employed if desired. Other suitable toothpaste formulations are described, for example, in U.S. Pat. No. 5,560,517.

As stated above, in the preferred toothpaste formulation of the present invention, antibiotic zeolite particles are separated from the deactivating ingredients of the formulation by a barrier composition. The barrier prevents contact of the zeolite particles with the deactivating agents, but is adapted to allow mixing of the particles with the rest of the formulation during brushing. Examples of barrier compositions that can be used include polyacrylic acid, sorbitol, polysorbate, starch, agar, carboxymethyl cellulose, PEG, and any suitable material, including polymeric materials, or in particular thermoplastic and thermosetting polymers.

Preferably, a gelling polymer is employed as a barrier layer. Carbopol is an appropriate gelling polymer that is commonly commercially available.

It is possible to employ barrier layers in several ways. For example, the barrier layer may be employed to microencapsulate individual particles of antimicrobial zeolite. Alternatively, several particles of antimicrobial zeolite may be distributed within each "drop" of a barrier material. For example, assemblages of several antibiotic zeolite particles can be coated with Carbopol. The coated particles are released from the coating upon brushing, the coatings being of a thickness to allow easy release of the particles, but to protect the silver in the particles from deactivating ingredients. It has been determined that such compositions are capable of exhibiting a long shelf life. It is also possible to microencapsulate individual antibiotic particles, e.g., in starch or agar, and to then incorporate the microencapsulated particles into another barrier layer, e.g., Carbopol. Where the inorganic antibiotic metal containing composition is a silver salt, the barrier layer can isolate the silver salt from inactivating ingredients.

Where antibiotic zeolite particles are microencapsulated, conventional microencapsulation compositions and techniques are employed. For example, it is possible to coat individual particles with starch, agar, or polymer using conventional methods such as spray drying, fluidized bed coating, electrostatic deposition, centrifugal extrusion, rotational suspension separation, polymerization at a phase boundary, pressure extrusion, or spraying into a solvent bath. Chemical processes of microencapsulation as also possible, such as complex coacervation, polymer-polymer incompatibility methods, interfacial polymerization, in-situ polymerization, in-liquid drying, thermal or ionic gelation, and desolvation in liquid media. Microencapsulation techniques usable to coat the antibiotic zeolites are well-known in the pharmaceutical industry, and include, for example, methods described in U.S. Pat. Nos. 5,503,851 and 5,393,533 among many other known methods.

It is preferable to physically separate all of the antibiotic zeolite from the deactivating parts of the formulation in the toothpaste dispensing device, e.g., to have the antibiotic portion of the formulation entirely separated from the deactivating parts in one continuous stripe. In this embodiment, the toothpaste can be formulated to administer at least two stripes containing separate ingredients per dose. Technology for manufacturing toothpastes containing such stripes is well known in this art, and described, e.g., in U.S. Pat. Nos. 5,324,505, 5,035,349, and 3,881,529.

The toothpaste of the invention has the capability of effecting substantial anti-microbial action during the time required for a normal toothbrushing. Ion release rate experiments show that the initial release rate of antibiotic zeolites in a typical concentration in toothpaste of, e.g., about 1%, can reach 25 parts per billion (ppb) per minute. At this rate, the minimum inhibitory concentration (MIC) for bacteria of about 2 ppb is reached in less than 5 seconds. This high rate of release generally occurs for about one minute following contact with water, after which a slower rate of release is exhibited.

Furthermore, it has been determined that ion release begins substantially at the time the toothpaste formulation is prepared. Therefore, at the time the toothpaste is applied to oral surfaces, significant amounts of antibiotic metal ion are available in the formulation to effect antimicrobial action, i.e., the concentration of antimicrobial metal ion is at or above the MIC.

One or more surfactants can be added to the toothpaste composition, in particular to aqueous slurries of antibiotic zeolite employed, to prevent aggregation. Suitable surfactants are well-known, and include, for example a mixture of sodium polyacrylate (e.g., 0.5 wt. %) and polysaccharide (e.g., 0.3 wt. %).

The coated zeolite particles employed in the aqueous formulations of the invention preferably have a particle diameter size of between 1 and 500, more preferably between about 1 and 300, most preferably between about 20 and 100 $\mu$m.

The uncoated zeolite particles preferably have a particle diameter size of from about 0.2 to 40 $\mu$m, more preferably between about 0.5 to 5 $\mu$m.

Antibiotic zeolites are well-known and can be prepared for use in the present invention using known methods. These include the antibiotic zeolites disclosed, for example, in U.S. Pat. Nos. 4,938,958 and 4,911,898.

Either natural zeolites or synthetic zeolites can be used to make the antibiotic zeolites used in the present invention. "Zeolite" is an aluminosilicate having a three dimensional skeletal structure that is represented by the formula: $XM2/nOAl_2O_3—YSiO_2—ZH_2O$. M represents an ion-exchangeable ion, generally a monovalent or divalent metal ion, n represents the atomic valency of the (metal) ion, X and Y represent coefficients of metal oxide and silica respectively, and Z represents the number of water of crystallization. Examples of such zeolites include A-type zeolites, X-type zeolites, Y-type zeolites, T-type zeolites, high-silica zeolites, sodalite, mordenite, analcite, clinoptilolite, chabazite and erionite. The present invention is not restricted to use of these specific zeolites.

The ion-exchange capacities of these zeolites are as follows: A-type zeolite=7 meq/g; X-type zeolite=6.4 meq/g; Y-type zeolite=5 meq/g; T-type zeolite=3.4 meq/g; sodalite= 11.5 meq/g; mordenite=2.6 meq/g; analcite=5 meq/g; clinoptilolite=2.6 meq/g; chabazite=5 meq/g; and erionite= 3.8 meq/g. These ion-exchange capacities are sufficient for the zeolites to undergo ion-exchange with ammonium and antibiotic metal ions.

The specific surface area of preferred zeolite particles is preferably at least 150 m²/g (anhydrous zeolite as standard) and the $SiO_2Al_2O_3$ mol ratio in the zeolite composition is preferably less than 14, more preferably less than 11.

The antibiotic metal ions used in the antibiotic zeolites should be retained on the zeolite particles through an ion-exchange reaction. Antibiotic metal ions which are adsorbed or attached without an ion-exchange reaction exhibit a decreased bacteriocidal effect and their antibiotic effect is not long-lasting. Nevertheless, it is advantageous for imparting quick antimicrobial action to maintain a sufficient amount of surface adsorbed metal ion.

In the ion-exchange process, the antibiotic metal ions tend to be converted into their oxides, hydroxides, basic salts etc. either in the micropores or on the surfaces of the zeolite and also tend to deposit there, particularly when the concentration of metal ions in the vicinity of the zeolite surface is high. Such deposition tends to adversely affect the bacteriocidal properties of ion-exchanged zeolite.

In an embodiment of the antibiotic zeolites, a relatively low degree of ion exchange is employed to obtain superior bacteriocidal properties. It is believed to be required that at least a portion of the zeolite particles retain metal ions having bacteriocidal properties at ion-exchangeable sites of the zeolite in an amount less than the ion-exchange saturation capacity of the zeolite. In one embodiment, the zeolite employed in the present invention retains antimicrobial metal ions in an amount up to 41% of the theoretical ion-exchange capacity of the zeolite. Such ion-exchanged zeolite with a relatively low degree of ion-exchange may be prepared by performing ion-exchange using a metal ion solution having a low concentration as compared with solutions conventionally used for ion exchange.

In antibiotic zeolite particles used in the present invention, ion-exchangeable ions present in zeolite, such as sodium ions, calcium ions, potassium ions and iron ions are preferably partially replaced with ammonium and antibiotic metal ions. Such ions may co-exist in the antibiotic zeolite particle since they do not prevent the bacteriocidal effect. While antibiotic metal ions include ions of silver, copper, zinc, mercury, tin, lead, bismuth, cadmium, chromium and thallium, edible antibiotic zeolites to be formulated into compositions to be used in the toothpaste of the invention include silver, gold, copper and zinc ions. These antibiotic metal ions can be used by themselves or in a mixture.

The antibiotic metal ion is preferably present in the range of from about 0.1 to 15wt. % of the zeolite. In one embodiment, the zeolite contain from 0.1 to 15wt. % of silver ions and from 0.1 to 8wt. % of copper or zinc ions. Although ammonium ion can be contained in the zeolite at a concentration of about 20 wt. % or less of the zeolite, it is desirable to limit the content of ammonium ions to from 0.5 to 15 wt. %, preferably 1.5 to 5 wt. %. Weight % described herein is determined for materials dried at 110° C., as this is the temperature employed for the preferred post-manufacturing drying process.

A preferred antibiotic zeolite for use in a toothpaste formulation is type A zeolite containing either a combination of ion-exchanged silver, zinc, and ammonium or silver and ammonium. One such zeolite is manufactured by Shinegawa, Inc. under the product number AW-10N and consists of 0.6% by weight of silver ion-exchanged in Type A zeolite particles having a diameter of about 2.5µ. Another formulation, AJ-10N, consists of about 2% by weight silver ion-exchanged in Type A zeolite particles having a diameter of about 2.5µ. Another formulation, AW-80, contains 0.6% by weight of silver ion-exchanged in Type A zeolite particles having a diameter of about 1.0µ. Another formulation, AJ-80N, consists of about 2% by weight silver ion-exchanged in Type A zeolite particles having a diameter of about 1.0µ. These zeolites preferably contain about between 0.5% and 2.5% by weight of ion-exchanged ammonium. The zeolites are often obtained in master batches of low density polyethylene, polypropylene, or polystyrene, containing 20 wt. % of the zeolite.

The antibiotic particles are preferably present in a concentration by weight in the toothpaste formulation of from 0.05 to 10%, more preferably from 0.1 to 5% by weight, and most preferably from 0.1 to 1%.

The antibiotic properties of the aqueous formulations of antibiotic zeolite particles of the invention may be assayed using conventional assay techniques, including for example determining the minimum growth inhibitory concentration (MIC) with respect to a variety of bacteria, eumycetes and yeast. In such a test, the bacteria listed below may be employed:

*Bacillus cereus* var *mycoides,*

*Escherichia coli,*

*Pseudomonas aeruginosa,*

*Staphylococcus aureus,*

*Streptococcus faecalis,*

*Aspergillus niger,*

*Aureobasiduim pullulans,*

*Chaetomium globosum,*

*Gliocladium virens,*

*Penicillum funiculosum,*

*Candida albicans,*

*Saccharomyces cerevisiae,*

The assay for determining MIC can be carried out by smearing a solution containing bacteria for inoculation onto a plate culture medium to which a test sample of the encapsulated antibiotic zeolite particles is added in a particular concentration, followed by incubation and culturing of the plate. The MIC is defined as a minimum concentration thereof required for inhibiting the growth of each bacteria.

The present invention will hereunder be explained in more detail with reference to the following non-limiting working examples.

EXAMPLE 1

Toothpaste Formulation Containing Antibiotic Zeolite Particles

A toothpaste formulation according to the present invention was prepared as follows.

An aqueous slurry was obtained of 20 wt. % type AW10 zeolite, the zeolite containing 0.6 wt. % Ag, 14 wt. % Zn, 2.5 wt. % ammonium, comprised of particles that are 2.5µm in diameter. A solution was prepared of 25 wt. % of the slurry, 10 wt. % carbopol, and water. The solution was blended thoroughly in a high shear mixer, a homogenizer, or an ultrasonic processor. Water was added to result in a final zeolite concentration of between 0.1 and 1 wt. %. A pH adjuster was added (sodium hydroxide) to increase pH of the solution to between 7 and 8. The solution was allowed to thicken to a paste-like consistency.

Conventional toothpaste ingredients were obtained to form the non-zeolite portion of the formulation. The conventional toothpaste ingredients were those sold under the "Crest" trademark (Procter and Gamble).

The zeolite containing portion and the zeolite-free portion of the formulation are combined in stripes using conventional striping technology. The resulting formulation maintains the antibiotic properties in a stable manner, affording a substantial shelf life.

For the tests described below, use of the toothpaste of the invention in oral care was simulated by mixing the toothpaste ingredients with water to result in a final concentration of between about 0.05 and 0.5 wt. % of antibiotic zeolite.

EXAMPLE 2

Toothpaste Formulation Containing Microencapsulated Zeolite

A toothpaste formulation of the invention is prepared containing microencapsulated particles.

Microencapsulated zeolite particles are prepared using a conventional spray drying apparatus to encapsulate the particles in starch or agar.

A 20% slurry of the microencapsulated zeolite particles is prepared by gradually adding the microencapsulated particles to water and carbopol (1–2 wt. %), and then gently mixing with a conventional laboratory paddle mixer to prevent rupture of the microencapsulation. The particles are allowed to stand for a sufficient time to allow thorough wetting of the particles by the solution, and are then gently mixed to create a uniform dispersion. Uniformity of the dispersion is judged by measuring clarity of the solution; the properly dispersed formulation is substantially clear as opposed to cloudy or white.

Water is added to obtain a final concentration of zeolite of between about 0.05 and 1 wt. %. Sodium hydroxide is added to increase the pH of the solution in order to thicken it to a paste-like consistency. Conventional toothpaste ingredients, such as those sold under the "Crest" trademark, are combined with the solution so as not to rupture the encapsulated zeolites. Conventional methods for making striped toothpaste are employed that maintain the zeolite containing portion and the conventional ingredients in physically separated stripes.

EXAMPLE 3

Microbiocidal Release from Toothpaste Containing Antibiotic Zeolite: Comparison with Control Toothpaste An in vitro microbial challenge was carried out to compare the toothpaste of the invention, prepared as described above, with a control formulation lacking antibiotic zeolites, for activity against *E. coli* and *S. aureus*. Nutrient broths containing the relevant stock culture solutions were directly inoculated onto filter discs to which the toothpastes had previously been applied. After incubation for 24 hours, the resulting surfaces were tested for viable bacteria. The filter disc with the toothpaste of the invention contained about 1700 CFU of *E. coli* and less than 100 CFU of *S. aureus*. The disc with the control toothpaste formulation contained about 89,000 CFU of *E. coli* and about 600,000 CFU of *S. aureus*. Thus, the toothpaste of the invention was greater than 98% effective in eliminating bacteria as compared with the control formulation.

EXAMPLE 4

Microbiocidal Release from Toothpaste Containing Antibiotic Zeolite

An in vitro microbial challenge was carried out to compare the toothpaste of the invention, prepared as described above, with a control composition lacking the antibiotic zeolite for activity against *E. coli* and *S. aureus* according to AATCC Test Method 90-1982. The toothpaste of the invention was found to exhibit a zone of inhibition of *E. coli* of 3.5 mm and of *S. aureus* of 6.5 mm. The control composition exhibited no inhibition. Thus, the toothpaste of the invention was found to inhibit *E. coli* and *S. aureus* to a substantially greater degree than the control composition.

EXAMPLE 5

Microbiocidal Release from Toothpaste Containing Antibiotic Zeolite: Comparison with Antibiotic Toothpaste Using Organic Antibiotic and Other Toothpastes An in vitro microbial challenge was carried out to compare the toothpaste of the invention, in slurry form prepared as described above, and in a powder form, with a commercially available toothpaste containing the organic antibiotic agent triclosan, with two commercially available toothpastes lacking an antibiotic agent (Toothpastes A and B), and with a control gel composition lacking antibiotic zeolite. Zone of inhibitions tests were conducted applying stock solutions of *S. aureus* and *B. gingivitis* to filter discs to which samples of the relevant toothpastes had previously been applied. The samples were incubated for 24 hours and the samples tested for viable bacteria. Results were determined in millimeters of inhibition. Dashes in the table below indicate that no test was done.

|  | S. Aureus | B. gingivitis |
|---|---|---|
| Toothpaste of the Invention (Slurry) | 23.5 | — |
| Toothpaste of the Invention (Powder) | 16.5 | 6.0 |
| Toothpaste with triclosan | 13.5 | — |
| Toothpaste A | 6.4 | — |
| Toothpaste B | 3.5 | — |
| Control | 3.0 | 0.5 |

These results show that the toothpaste of the invention is at least as effective as, if not more effective than, commercially available toothpaste containing triclosan at inhibiting *S. aureus*, while avoiding use of an organic antibiotic agent. The toothpaste of the invention was also substantially more effective at inhibiting *S. aureus* than either of the commercially available toothpastes that lacked an antibiotic agent. The toothpaste of the invention was substantially more effective at inhibiting *B. gingivitis* than was the control composition.

EXAMPLE 6

Safety and Biocompatibility

Safety and biocompatibility tests were conducted on the antibiotic zeolites employed in the invention. ISO 10993-1 procedures were employed. The following results were obtained:

---
Cytotoxicity: Non-Toxic
Acute Systemic Toxicity: Non-Toxic
Intracutaneous Toxicity: Passed
Skin Irritation Test: Non-Irritant
Chronic Toxicity: No Observable Effect
In-vitro Hemolysis: Non-Hemolytic
30-day Muscle Implant Test: Passed
60-day Muscle Implant Test: Passed
90-day Muscle Implant Test: Passed
Arnes Mutagenicity Test: Passed
Pyrogenicity: Non-Pyrogenic
---

An oral biocompatibility test was also conducted using the relevant ISO 10993-1 procedure. Oral administration of the zeolite containing material at the maximum level that was technically feasible resulted in an $LD_{50}$ value that was superior to that found for common table salt.

Thus, the antibiotic zeolites are exceptionally suitable under relevant toxicity and biocompatibility standards for use in a toothpaste.

While preferred embodiments of the invention have been described in the foregoing examples, it will be understood by those skilled in the art that various changes and modifications may be made therein without departing from the spirit and the scope of the invention. Accordingly, the above description should be construed as illustrating and not limiting the scope of the invention.

What is claimed is:

1. A toothpaste formulation having antimicrobial properties comprising:
   an antimicrobial agent comprising ceramic particles comprising antimicrobial metal ions;
   at least one ingredient capable of inactivating said antimicrobial metal ions;
   said antimicrobial agent being disposed within an aqueous based paste or gel forming a barrier layer separating said metal ions from said at least one ingredient, said metal ions being released imparting substantial antimicrobial action to an oral surface upon contact with said oral surface during normal toothbrushing.

2. The toothpaste formulation of claim 1 wherein said barrier layer is in the form of a continuous stripe separating said metal ions from said at least one ingredient capable of inactivating said antimicrobial metal ions.

3. A toothpaste formulation having antimicrobial properties comprising:
   an antimicrobial agent comprising antimicrobial ceramic particles comprising antimicrobial metal ions;
   at least one ingredient capable of inactivating said antimicrobial metal ions;
   said agent being dispersed within a barrier layer separating said metal ions from said at least one ingredient capable of inactivating said antimicrobial metal ions, said metal ions being released imparting substantial antimicrobial action to an oral surface upon contact with said oral surface during normal toothbrushing.

4. The toothpaste formulation of claim 3 wherein said antimicrobial ceramic particles comprise zeolite containing silver cations as the active ingredient.

5. The toothpaste formulation of claim 3 wherein said antimicrobial ceramic particles are encapsulated in said barrier layer.

6. The toothpaste formulation of claim 5 wherein said barrier layer comprises an aqueous based paste or gel.

7. The toothpaste formulation of claim 6 wherein said antimicrobial ceramic particles are coated with said aqueous based paste or gel.

8. The toothpaste formulation of claim 1 wherein said barrier layer is a gel polymer.

9. The toothpaste formulation of claim 1 wherein said barrier layer is comprised of a material selected from the group consisting of polyacrylic acid, sorbitol, polysorbate, starch, agar, carboxymethyl cellulose, PEG, thermoplastic polymers, and thermosetting polymers.

10. The toothpaste formulation of claim 1 wherein said antimicrobial ceramic particles comprise antimicrobial zeolite prepared by replacing all or part of the ion-exchangeable ions in said zeolite with an antimicrobial metal ion.

11. The toothpaste formulation of claim 10 wherein said antimicrobial metal ion is selected from the group consisting of silver, copper, zinc, and gold.

12. The toothpaste formulation of claim 11 wherein said antimicrobial metal ion is silver.

13. The toothpaste formulation of claim 1 wherein said antimicrobial ceramic particles are encapsulated in a polymeric gel.

14. The toothpaste formulation of claim 1 wherein said antimicrobial ceramic particles are selected from the group consisting of zeolite, hydroxyapatite, and zirconium phosphate.

15. The toothpaste formulation of claim 14 wherein said antimicrobial ceramic particles comprise type A zeolite particles ion-exchanged with silver in an amount of from about 0.1 to 1 5wt. % of the zeolite and have a diameter of from about 0.5 to 5 µm.

16. The toothpaste formulation of claim 10 containing greater than about 0.5% by weight of ion-exchanged ammonium.

17. The toothpaste formulation of claim 10 containing a zeolite concentration of between about 0.1 and 1 wt. %.

18. The toothpaste formulation of claim 15 wherein said type A zeolite comprises unexchanged antimicrobial metal ions present on the surface of said zeolite to impart quick acting antimicrobial activity upon toothbrushing.

* * * * *